(12) United States Patent
Finan et al.

(10) Patent No.: US 11,147,920 B2
(45) Date of Patent: Oct. 19, 2021

(54) DIABETES MANAGEMENT SYSTEM WITH AUTOMATIC BASAL AND MANUAL BOLUS INSULIN CONTROL

(71) Applicant: LifeScan IP Holdings, LLC, Malvern, PA (US)

(72) Inventors: Daniel Finan, Philadelphia, PA (US); Thomas McCann, Jr., Pottstown, PA (US)

(73) Assignee: LifeScan IP Holdings, LLC, Malvern, PA (US)

( * ) Notice: Subject to any disclaimer, the term of this patent is extended or adjusted under 35 U.S.C. 154(b) by 97 days.

(21) Appl. No.: 15/489,773

(22) Filed: Apr. 18, 2017

(65) Prior Publication Data

US 2018/0296757 A1  Oct. 18, 2018

(51) Int. Cl.
*A61M 5/172* (2006.01)
*A61M 5/142* (2006.01)
*A61M 5/178* (2006.01)

(52) U.S. Cl.
CPC .......... *A61M 5/1723* (2013.01); *A61M 5/142* (2013.01); *A61M 5/14244* (2013.01);
(Continued)

(58) Field of Classification Search
CPC ................ A61M 5/1723; A61M 5/003; A61M 5/14244; A61M 5/14248; A61M 2005/1726; A61M 2005/14208; A61M 2005/14264; A61M 2005/14268; A61M 2230/201; A61M 2205/3303;
(Continued)

(56) References Cited

U.S. PATENT DOCUMENTS 6,179,979 B1  1/2001  Hodges et al.
6,444,115 B1  9/2002  Hodges et al.
(Continued)

FOREIGN PATENT DOCUMENTS

WO   2012051344 A2   4/2012

OTHER PUBLICATIONS

Atlas et al., "MD-Logic Artificial Pancreas System," Diabetes Care, vol. 33, No. 5, May 2010.
(Continued)

*Primary Examiner* — Lauren P Farrar
*Assistant Examiner* — Hamza A Darb
(74) *Attorney, Agent, or Firm* — Barclay Damon LLP (57) ABSTRACT

Systems and methods for diabetes management with automatic basal and manual bolus insulin control are presented. An exemplary system includes a delivery device, a glucose sensor, and a controller. The delivery device delivers insulin and the glucose sensor measures glucose levels of the subject. A basal insulin dose is calculated using a model predictive control algorithm and physiological data of the subject including desired glucose levels, amounts of the delivered insulin and the measured glucose levels. A manual bolus insulin dose is initiated by the subject. The manual bolus insulin dose is modified based on one or both of the model predictive control algorithm and the physiological data of the subject. A total insulin dose is determined based on the modified manual bolus insulin dose and the calculated basal insulin dose, and delivered to the subject.

10 Claims, 3 Drawing Sheets

(52) U.S. Cl.
CPC ..... *A61M 5/178* (2013.01); *A61M 2005/1726* (2013.01); *A61M 2205/3584* (2013.01); *A61M 2205/3592* (2013.01); *A61M 2205/505* (2013.01); *A61M 2230/201* (2013.01)

(58) Field of Classification Search
CPC .................. A61M 5/178; A61M 5/142; A61M 2205/3592; A61M 2205/3584; A61M 2205/505; G16H 20/17; A61B 5/4839; A61B 5/14532
See application file for complete search history.

(56) References Cited

U.S. PATENT DOCUMENTS

| | | | |
|---|---|---|---|
| 7,060,059 | B2 | 6/2006 | Keith et al. |
| 7,276,029 | B2 | 10/2007 | Goode, Jr. et al. |
| 8,163,162 | B2 | 4/2012 | Chatelier et al. |
| 8,562,587 | B2 | 10/2013 | Kovatchev et al. |
| 8,762,070 | B2 | 6/2014 | Doyle, III et al. |
| 2006/0167345 | A1 | 7/2006 | Vespasiani |
| 2011/0054439 | A1 | 3/2011 | Yodfat et al. |
| 2011/0257627 | A1 | 10/2011 | Hovorka |
| 2011/0313680 | A1 | 12/2011 | Doyle, III et al. |
| 2012/0238854 | A1 | 9/2012 | Blomquist et al. |
| 2013/0231642 | A1 | 9/2013 | Doyle, III et al. |
| 2013/0338630 | A1 | 12/2013 | Agrawal et al. |
| 2013/0345663 | A1 | 12/2013 | Agrawal et al. |
| 2014/0005633 | A1* | 1/2014 | Finan ................ A61M 5/1723 604/504 |
| 2014/0046159 | A1 | 2/2014 | Kovatchev et al. |
| 2014/0066892 | A1 | 3/2014 | Keenan et al. |
| 2014/0081236 | A1 | 3/2014 | Wilinska et al. |
| 2014/0114278 | A1* | 4/2014 | Dobbles ................ G16H 40/63 604/504 |
| 2014/0180203 | A1 | 6/2014 | Budiman et al. |
| 2014/0180240 | A1 | 6/2014 | Finan et al. |
| 2014/0200559 | A1 | 7/2014 | Doyle, III et al. |
| 2015/0141912 | A1 | 5/2015 | Estes |
| 2015/0157792 | A1 | 6/2015 | Chovanda et al. |

OTHER PUBLICATIONS

Cobelli et al., "Artificial Pancreas: Past, Present, Future" Diabetes vol. 60, Nov. 2011.

Kovatchev et al., "Control to Range for Diabetes: Functionality and Modular Architecture," J. Diabetes Sci. Techn., vol. 3, Issue 5, Sep. 2009.

Lee et al., "A Closed-Loop Artificial Pancreas based on MPC: Human Friendly Identification and Automatic Meal Disturbance Rejection," Proceedings of the 17th World Congress, The International Federation of Automatic Control, Seoul Korea Jul. 6-11, 2008.

Lee et al., "A Closed-Loop Artificial Pancreas Using Model Predictive Control and a Sliding Meal Size Estimator" J. Diabetes Sci. Techn., vol. 3, Issue 5, Sep. 2009.

Magni et al., "Model Predictive Control of Type 1 Diabetes: An in Silico Trial" J. Diabetes Sci. Techn., vol. 1, Issue 6, Nov. 2007.

Magni et al., "Run-to-Run Tuning of Model Predictive Control for Type 1 Diabetes Subjects: In Silico Trial" J. Diabetes Sci. Techn., vol. 3, Issue 5, Sep. 2009.

Soru et al., "MPC Based Artificial Pancreas; Strategies for Individualization and Meal Compensation," Annual Reviews in Control 36, p. 118-128 (2012).

Percival et al., "Closed-Loop Control and Advisory Mode Evaluation of an Artificial Pancreatic Beta Cell: Use of Proportional-Integral-Derivative Equivalent Model-Based Controllers" J. Diabetes Sci. Technol., vol. 2, Issue 4, Jul. 2008.

Percival et al., "Closed-Loop Control of an Artificial Pancreatic β-Cell Using Multi-Parametric Model Predictive Control," Diabetes Res. 2008.

Wang et al., "Automatic Bolus and Adaptive Basal Algorithm for the Artificial Pancreatic β-Cell" Diabetes Techn. Ther., vol. 12, No. 11, 2010.

International Search Report and Written Opinion issued in corresponding International Patent Application No. PCT/US2018/26208, dated Jul. 6, 2018, 10 pages.

* cited by examiner

DIABETES MANAGEMENT SYSTEM WITH AUTOMATIC BASAL AND MANUAL BOLUS INSULIN CONTROL

TECHNICAL FIELD

This invention is generally directed to the field of diabetes management systems and more specifically to a system and related method for insulin control, including both automatic basal insulin control and manual bolus insulin control.

BACKGROUND

Diabetes mellitus is a chronic metabolic disorder caused by an inability of the pancreas to produce sufficient amounts of the hormone insulin, resulting in the decreased ability of the body to metabolize glucose. This failure leads to hyperglycemia or the presence of an excessive amount of glucose in the blood plasma. Persistent hyperglycemia alone or in combination with hypoinsulinemia is associated with a variety of serious symptoms and life threatening long term complications. Because restoration of endogenous insulin production is not yet possible, a permanent therapy is necessary which provides constant glycemic control in order to always maintain the level of blood glucose within normal limits. Such glycemic control is achieved by regularly supplying external insulin to the body of the patient to thereby reduce the elevated levels of blood glucose.

Substantial improvements in diabetes therapy have been achieved by the development of drug delivery devices, relieving the patient of the need for syringes or drug pens for the administration of multiple daily injections. These drug delivery devices allow for the delivery of the drug in a manner that bears greater similarity to the naturally occurring physiological processes and can be controlled to follow standard or individually modified protocols to give the patient better glycemic control.

These drug delivery devices can be constructed as implantable devices. Alternatively, the delivery device may be an external device with an infusion set for subcutaneous infusion to the patient via the transcutaneous insertion of a catheter, cannula or a transdermal drug transport such as through a patch. The external drug delivery devices may be mounted on clothing or, and more preferably, hidden beneath or inside clothing, or mounted on the body and are generally controlled via a user interface built into the device or on a separate remote device.

Blood or interstitial analyte monitoring is required to achieve acceptable glycemic control with the devices. For example, delivery of suitable amounts of insulin by the drug delivery device requires that the patient frequently determines his or her blood glucose level. The level may be input into the delivery device, or pump, or on a controller, after which suitable modification may be calculated to the default or currently in-use insulin delivery protocol, i.e. dosage and timing, which modification is used to adjust the drug delivery device operation accordingly. Alternatively, or in conjunction with episodic glucose determination, continuous glucose monitoring ("CGM") may be used with drug delivery devices, which CGM allows for closed loop control of the insulin being infused into the diabetic patients.

To allow for closed-loop control, autonomous modulation of the drug being delivered to the user is provided by a controller using one or more algorithms. For example, a proportional-integral-derivative algorithm ("PID") controller that are reactive to observed glucose levels may be utilized, which controllers can be tuned based on simple rules of the mathematical models of the interaction between glucose and insulin in a person.

Alternatively, a model predictive algorithm ("MPC") controller may be used. The MPC controller is advantageous as compared to the PID controller because the MPC proactively considers the near future effects of control changes, sometimes subject to constraints, in determining the output of the MPC, whereas PID typically involves only past outputs in determining future changes. Constraints can be implemented in the MPC controller such that a solution is in a confined "space", meaning within imposed delivery limitations, is guaranteed and the system is prevented from exceeding a limit that has been reached. Known MPCs are described in the following documents: U.S. Pat. No. 7,060,059; U.S. Patent Application Nos. 2011/0313680, 2011/0257627, and 2014/0180240; International Publication WO 2012/051344; Percival et al., "Closed-Loop Control and Advisory Mode Evaluation of an Artificial Pancreatic β-Cell: Use of Proportional-Integral-Derivative Equivalent Model-Based Controllers," J. Diabetes Sci. Techn., Vol. 2, Issue 4, July 2008; Paola Soru et al., "MPC Based Artificial Pancreas; Strategies for Individualization and Meal Compensation," Annual Reviews in Control 36, p. 118-128 (2012); Cobelli et al., "Artificial Pancreas: Past, Present, Future," Diabetes, Vol. 60, November 2011; Magni et al., "Run-to-Run Tuning of Model Predictive Control for Type 1 Diabetes Subjects: In Silico Trial," J. Diabetes Sci. Techn., Vol. 3, Issue 5, September 2009; Lee et al., "A Closed-Loop Artificial Pancreas Using Model Predictive Control and a Sliding Meal Size Estimator," J. Diabetes Sci. Techn., Vol. 3, Issue 5, September 2009; Lee et al., "A Closed-Loop Artificial Pancreas based on MPC: Human Friendly Identification and Automatic Meal Disturbance Rejection," Proceedings of the 17th World Congress, The International Federation of Automatic Control, Seoul Korea Jul. 6-11, 2008; Magni et al., "Model Predictive Control of Type 1 Diabetes: An in Silico Trial," J. Diabetes Sci. Techn., Vol. 1, Issue 6, November 2007; Wang et al., "Automatic Bolus and Adaptive Basal Algorithm for the Artificial Pancreatic β-Cell," Diabetes Techn., Vol. 12, No. 11, 2010; Percival et al., "Closed-Loop Control of an Artificial Pancreatic β-Cell Using Multi Parametric Model Predictive Control" Diabetes Research 2008; Kovatchev et al., "Control to Range for Diabetes: Functionality and Modular Architecture," J. Diabetes Sci. Techn., Vol. 3, Issue 5, September 2009; and Atlas et al., "MD-Logic Artificial Pancreas System," Diabetes Care, Vol. 33, No. 5, May 2010. All articles or documents cited in this application are hereby incorporated by reference into this application as if fully set forth herein.

DETAILED DESCRIPTION

As used herein, the terms "about" or "approximately" for any numerical values or ranges indicate a suitable dimensional tolerance that allows the part or collection of components to function for its intended purpose as described herein. In addition, as used herein, the terms "patient,"

"user," and "subject" refer to any human or animal subject and are not intended to limit the systems or methods to human use, although use of the subject techniques in a human patient represents a preferred embodiment.

The present invention relates, in part, to diabetes management systems that combine automatic basal insulin control with manual bolus insulin control. Automatic basal insulin control through a controller using an MPC algorithm, or another autonomous modulating algorithm, may fail to account for manual bolus doses of insulin initiated by a subject. Manual boluses may be calculated by the subject using a bolus calculator, which uses an insulin-on-board model, insulin sensitivity factor of the subject, current glucose levels, and target glucose levels. In such a system, each of these two processes, namely automatic basal insulin control and manual bolus insulin control, proceed independently, even where there is a directional contradiction between the two models. The lack of correlation between these processes can lead to issues, such as the delivery of excessive insulin to the subject, leading to a hypoglycemic excursion.

One way of overcoming these limitations is to bridge the gap between manual bolus insulin control and automatic basal insulin control by allowing some or all of the data from the automatic process, such as physiological data including trends and rates of change thereof, to be used to modify, cancel, or change a bolus commanded by the subject through the manual process. Advantageously, the present disclosure provides, in part, techniques for combining both automatic basal insulin control and manual bolus insulin control so that contradictions between the models are resolved in a manner consistent with patient safety.

As another advantage, the techniques set forth herein may be viewed as an enhancement to conventional autonomous modulating control algorithms, such as MPC. to allow for a more fully automated artificial pancreas that combines both basal and bolus control.

Generally stated, provided herein, in one embodiment, is a diabetes management system with automatic basal and manual bolus insulin control. The diabetes management system includes a delivery device, a glucose sensor, and a controller. The delivery device is for delivering insulin to a subject. The glucose sensor is for measuring glucose levels of the subject. The controller is configured to receive glucose levels of the subject from the glucose sensor. The controller is configured to automatically calculate a basal insulin dose using a model predictive control algorithm ("MPC") of the subject based on physiological data of the subject including desired glucose levels, amounts of the delivered insulin and the measured glucose levels of the subject. The controller is configured to receive a manual bolus insulin dose initiated by the subject. The controller is configured to modify the manual bolus insulin dose based on the physiological data of the subject. The controller is configured to determine a total insulin dose based on the modified manual bolus insulin dose and the calculated basal insulin dose. In one embodiment, the controller may be configured to deliver the basal insulin dose automatically (i.e., without patient confirmation) and bolus insulin dose upon confirmation to the subject. In another embodiment, the controller may instruct the patient to cancel the bolus insulin dose, e.g., by annunciating the instruction to the patient. In a further embodiment, the controller may only modify the basal insulin dose responsive to the bolus dose.

In another embodiment, a diabetes management system with automatic basal and manual bolus insulin control is presented. The diabetes management system includes a delivery device, a glucose sensor, and a controller. The controller is configured to receive glucose levels of the subject from the glucose sensor. The controller is configured to automatically calculate a basal insulin dose using MPC, or other autonomous control algorithm, of the subject based on physiological data of the subject including desired glucose levels, amounts of the delivered insulin and the measured glucose levels. The controller is configured to receive a manual bolus insulin dose initiated by the subject. The controller is configured to modify the manual bolus insulin dose based on the autonomous control algorithm and the physiological data of the subject.

In a further embodiment, a method for managing diabetes using automatic basal and manual bolus insulin control is presented using a delivery device for delivering insulin to a subject and a glucose sensor for measuring glucose levels of the subject. Glucose levels of the subject are received from the glucose sensor. A basal insulin dose is automatically calculated using autonomous algorithm control of the subject, such as MPC, based on physiological data of the subject including desired glucose levels, amounts of the delivered insulin and the measured glucose levels. A manual bolus insulin dose initiated by the subject is received. The manual bolus insulin dose is modified based on the physiological data of the subject. A total insulin dose is determined based on the modified manual bolus insulin dose and the calculated basal insulin dose. For example, the delivery device may be commanded to deliver the total insulin dose to the subject. In another example, the basal dose may be canceled, and the patient may be instructed to cancel the bolus insulin dose.

The above embodiments are intended to be merely examples. It will be readily apparent from the following discussion that other embodiments are within the scope of the disclosed subject matter.

Figure 1:
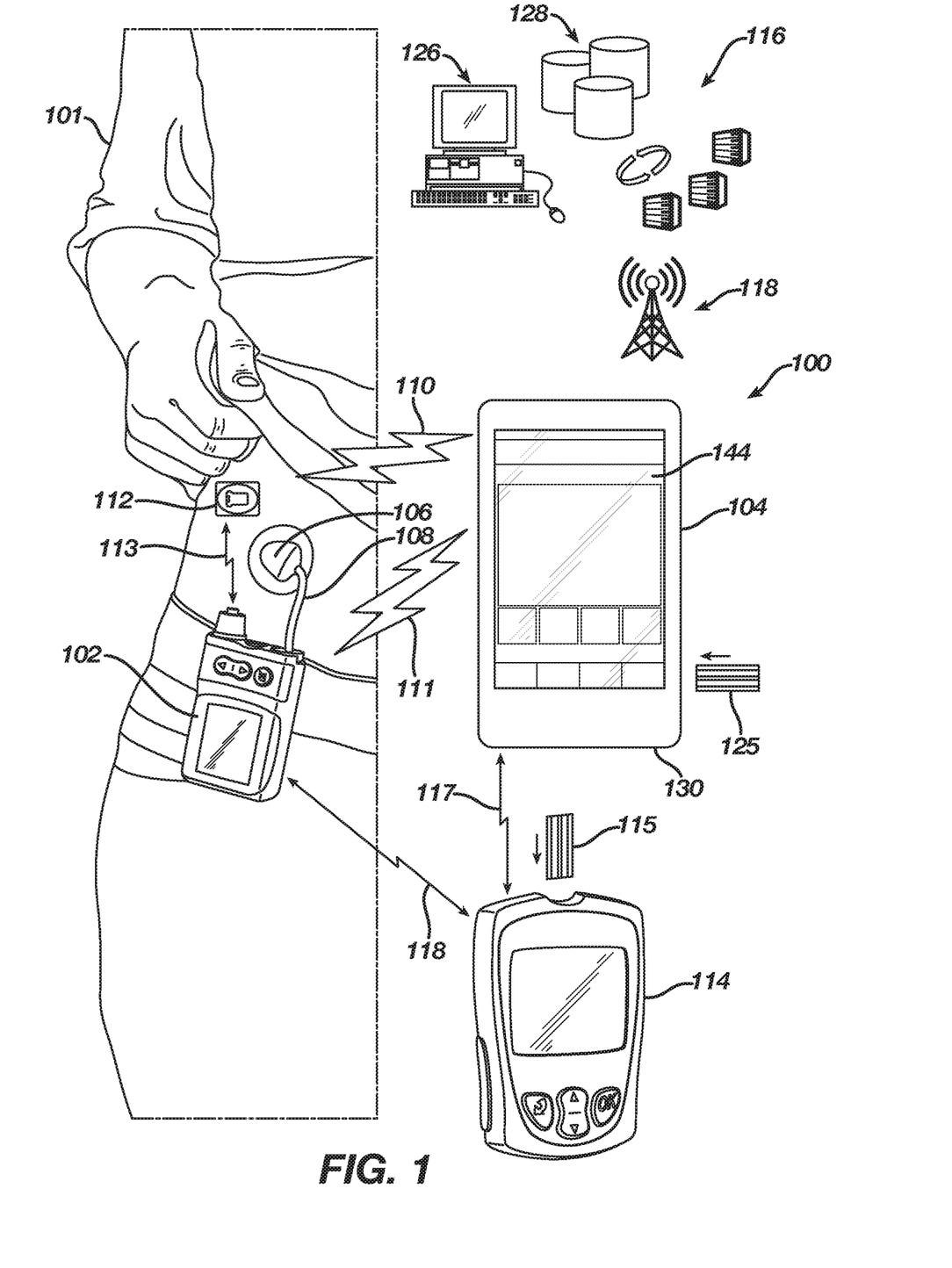
FIG. 1 illustrates a diabetes management system, in accordance with aspects of the present disclosure.

Specific working examples will now be described with respect to FIGS. 1-3. FIG. 1 illustrates a diabetes management system 100, which may be viewed as an artificial pancreas, according to this embodiment. The diabetes management system 100 includes a drug delivery device 102 and a controller 104. The drug delivery device 102 is connected to an infusion set 106 via flexible tubing 108. Various embodiments of the invention can also be used with injections via syringe or insulin pen instead of, or in addition to, infusion via the drug delivery device 102.

The drug delivery device 102 is configured to transmit and receive data to and from the controller 104 by, for example, a communications link 111 such as radio frequency ("RF"), BLUETOOTH® or the like. In one embodiment, the drug delivery device 102 is an insulin infusion device, or pump, and the controller 104 may be a hand-held portable controller, or a consumer electronic device, such as a smart phone, computer, exercise or user monitoring device, or the like. In such an embodiment, data transmitted from the drug delivery device 102 to the controller 104 may include information such as, for example, insulin delivery data, blood glucose information, basal, bolus, insulin to carbohydrates ratio or insulin sensitivity factor. The controller 104 can be configured to include a closed-loop controller that has been programmed to receive continuous glucose readings from a CGM sensor 112 via a communications link 110. Data transmitted from the controller 104 to the drug delivery device 102 may include glucose test results and a food database to allow the drug delivery device 102 to calculate the amount of insulin to be delivered by the drug delivery device 102. Alternatively, the controller 104 may perform basal dosing or bolus calculation and send the results of such calculations to the drug delivery device. Bolus calculation may be done manually upon initiation by the subject, or may be automated so that the system is capable of incorporation of both bolus and basal insulin control.

A glucose meter 114 (e.g., an episodic blood-glucose meter), alone or in conjunction with the CGM sensor 112, provides data to either or both of the controller 104 and drug delivery device 102, e.g., via a communications links 117 and 118. The glucose meter 114 can measure a fluid sample placed on a test strip 115. The two hatched areas on the test strip 115 graphically represent two electrodes, as discussed below. The controller 104 can present information and receive commands via a user interface, such as the displayed touchscreen 144, or other devices. The CGM sensor 112 can provide data, e.g., current blood-glucose values, directly to the drug delivery device 102 via a communications link 113.

The controller 104, the drug-delivery device 102, and the CGM sensor 112 can be integrated into multi-function units in any combination. For example, the controller 104 can be integrated with the drug-delivery device 102 to form a combined device with a single housing. Infusion, sensing, and controlling functions can also be integrated into a monolithic artificial pancreas. In various embodiments, the controller 104 is combined with the glucose meter 114 into an integrated monolithic device having a housing. In other embodiments, the controller 104 and the glucose meter 114 are two separable devices that are dockable with each other to form an integrated device. Each of the devices 102, 104, and 114 has a suitable micro-controller (not shown for brevity) programmed to carry out various functionalities.

The drug delivery device 102 or the controller 104 can also be configured for bi-directional communication with a remote health monitoring station 116 through, for example, a communication network 118. One or more servers 126 or storage devices 128 can be communicatively connected to the controller 104 via the network 118. In an example, the drug delivery device 102 communicates with a personal computer (e.g., the controller 104) via a communication link, such as RF, BLUETOOTH, or the like. The controller 104 and the remote station 116 also can be configured for bi-directional wired communication through, for example, a telephone land based communication network. Examples of remote monitoring stations 116 may include, but are not limited to, a personal or networked computer 126, a server 128 to a memory storage, a personal digital assistant, mobile telephone, a hospital based monitoring station or a dedicated remote clinical monitoring station. Alternatively, and though not shown in FIG. 1, storage, for example, the control algorithm, may further be provided in the cloud.

The control algorithm can reside in the remote controller 104, in the drug delivery device 102, or both in the configurations shown in FIG. 1. In one configuration, the controller 104 will wirelessly gather the necessary information (e.g., insulin history) from the drug delivery device 102, as well as from the glucose sensor 112 (e.g., glucose data) to allow the drug delivery device 102, using the control algorithm, to calculate the amount of insulin to be modulatively delivered by the drug delivery device 102. Alternatively, the controller 104 includes the control algorithm and may perform basal dosing or bolus calculation and send the results of such calculations along with delivery instructions to the drug delivery device 102. In an alternative embodiment, an episodic blood glucose meter 114 and biosensors 115 also may be used alone or in conjunction with the CGM sensor 112 to provide blood glucose data to either or both of the controller 104 and the drug delivery device 102. The glucose meter 114 can measure the current through the electrodes on the biosensor 115 to determine the glucose level of the fluid sample. Exemplary glucose sensors and associated components are shown and described in U.S. Pat. Nos. 6,179,979, 8,163,162, and 6,444,115, which are incorporated by reference herein in their entireties. Exemplary CGM sensors utilize amperometric electrochemical sensor technology to measure an analyte. The CGM sensor 112 may include three electrodes operably connected to the sensor electronics and covered by a sensing membrane and a biointerface membrane, which are attached by a clip. The top ends of the electrodes are in contact with an electrolyte phase (not shown), which is a free-flowing fluid phase disposed between the sensing membrane and the electrodes. The sensing membrane may include an enzyme, e.g., analyte oxidase, which covers the electrolyte phase. Details of the sensor and associated components are shown and described in U.S. Pat. No. 7,276,029, which is incorporated by reference herein.

The drug delivery device 102 can include any or all of: electronic signal processing components including a central processing unit and memory elements for storing control programs and operation data, a communications module (not shown) for sending and receiving communication signals (e.g., messages), a display for providing operational information to the user, a plurality of navigational buttons for the user to input information, a battery for providing power to the system, an alarm (e.g., visual, auditory or tactile) for providing feedback to the user, a vibrator for providing feedback to the user, and a drug delivery mechanism (e.g., a drug pump and drive mechanism) for forcing insulin from an insulin reservoir (e.g., an insulin cartridge) through a side port connected via the flexible tubing 108 to an infusion set 106 and into the body of the user.

Various glucose management systems include an episodic glucose sensor (e.g., a glucose meter 114) and an infusion pump. An example of such a system is ONETOUCH PING® Glucose Management System manufactured by the Animas Corporation. The "ezBG" feature of this system can compute a correction bolus amount of insulin to be delivered by the infusion pump using the results of an episodic glucose measurement. The pump and meter communicate wirelessly. Another example is the ANIMAS VIBE insulin pump, which communicates with a Dexcom, Inc. G4® or G5® CGM system. Interfaces can be provided to connect these components. Closed-loop, autonomous control algorithms can be programmed in, e.g., the MATLAB language to regulate the rate of insulin delivery based on the glucose level of the patient, historical glucose measurement and anticipated future glucose trends, and patient specific information.

In an example, the drug delivery device 102 is an insulin pump that communicates directly with the CGM sensor 112 via the link 113. The drug delivery device 102 includes control functions to compute delivery amounts of insulin using blood glucose data from the CGM sensor 112. The controller 104 is a smartphone running an application (downloadable software application) that communicates with the drug delivery device 102 via the link 111 to provide functions for remote operation of the drug delivery device 102 and remote monitoring of blood glucose. The application can perform functions to calculate boluses or adjust insulin delivery amounts.

The controller 104 may include one or more data processors that implement processes of various embodiments described herein. A "data processor" is a device for processing data and can include a central processing unit (CPU), a desktop computer, a laptop computer, a mainframe computer, a personal digital assistant, a digital camera, a cellular phone, a smartphone, or any other device for processing data, managing data, or handling data, whether implemented with electrical, magnetic, optical, biological components, or otherwise. The control 104 may have or provide subsystems such as a peripheral system, a user interface, and a storage device, which may be integrated within the controller 104 or may be implemented as stand-alone components.

Program code to carry out methods described herein can execute entirely on a single processor or on multiple communicatively-connected processors. For example, code can execute wholly or partly on a user's computer and wholly or partly on a remote computer, e.g., a server. The remote computer can be connected to the user's computer through the network 118. The user's computer or the remote computer can be non-portable computers, such as conventional desktop personal computers (PCs), or can be portable computers such as tablets, cellular telephones, smartphones, or laptops. The peripheral system can include one or more devices configured to provide digital content records or other data to the controller 104. For example, a biosensor such as a test strip 115 can be connected to the controller 104 via the peripheral system, e.g., using a Bluetooth Smart or other wireless link. The biosensor can also be directly connected to the controller 104. The peripheral system can also include digital still cameras, digital video cameras, cellular phones, or other data processors. The peripheral system can also include one or more bus bridges, e.g., to communicatively connect devices having USB, FIREWIRE, RS-232, or other interfaces to the controller 104. The controller 104, upon receipt of data from a device in the peripheral system, can store that data in the storage device 128.

The controller 104 is communicatively connected to the user interface displayed as touch screen 144 or, in the alternative, the user interface can be or include a mouse, a keyboard, another computer (connected, e.g., via a network or a null-modem cable), a microphone and speech processor or other devices for receiving voice commands, a camera and image processor or other devices for receiving visual commands, e.g., gestures, or any device or combination of devices.

The controller 104 can send messages and receive data, including program code, to and from the network 118. For example, requested code for an application program (e.g., a JAVA applet) can be stored on a tangible non-volatile computer-readable storage medium connected to the network 118. A network server 128 can retrieve the code from the medium and transmit it via the network 118. The received code can be executed by the controller 104 as it is received, or stored for later execution.

The controller 104 can be configured to operate in an open-loop mode. In this operating mode, the system behaves like a traditional, open-loop controlled insulin pump. Insulin is delivered according to a patient-set basal rate profile and patient-calculated meal and correction boluses. CGM data can be recorded and displayed for patient information, but are not used for automated insulin calculations. Similar functions are provided by, e.g., the ANIMAS VIBE insulin pump with a DEXCOM G4 CGM system.

The controller 104 can also be configured to operate in a closed-loop mode. In this operating mode, the controller 104 commands the drug delivery device 102 to deliver the patient's pre-set basal rates modulated, if necessary, by a predictive closed-loop control algorithm that uses as one of its inputs the glucose values communicated by the CGM sensor 112, the glucose meter 114, or both at specific time intervals e.g., every five minutes. This permits reducing the probability of hypoglycemic excursions beyond a low glucose limit or hyperglycemic excursions beyond a high glucose limit. Users can calculate meal and correction boluses. The controller 104 can be configured to provide a bolus calculator via the user interface of the touchscreen 144 to assist users in determining bolus insulin amounts. The closed-loop control algorithm can take these manual boluses into account in forming an insulin-on-board ("IOB") estimate, and then can use the IOB estimate to determine how much additional insulin is required to process a detected level of blood glucose.

The controller 104 can also be configured to operate in a maintenance mode in which low-level control of the drug delivery device 102 is provided via the user interface of the touchscreen 144 or other user interface. Control of other functions not typically accessed by patients can also be provided. This mode can permit testing of the controller 104, the drug delivery device 102, or the glucose meter 114 during manufacturing or, e.g., when the controller 104 and the glucose meter 114 require service.

Figure 2:
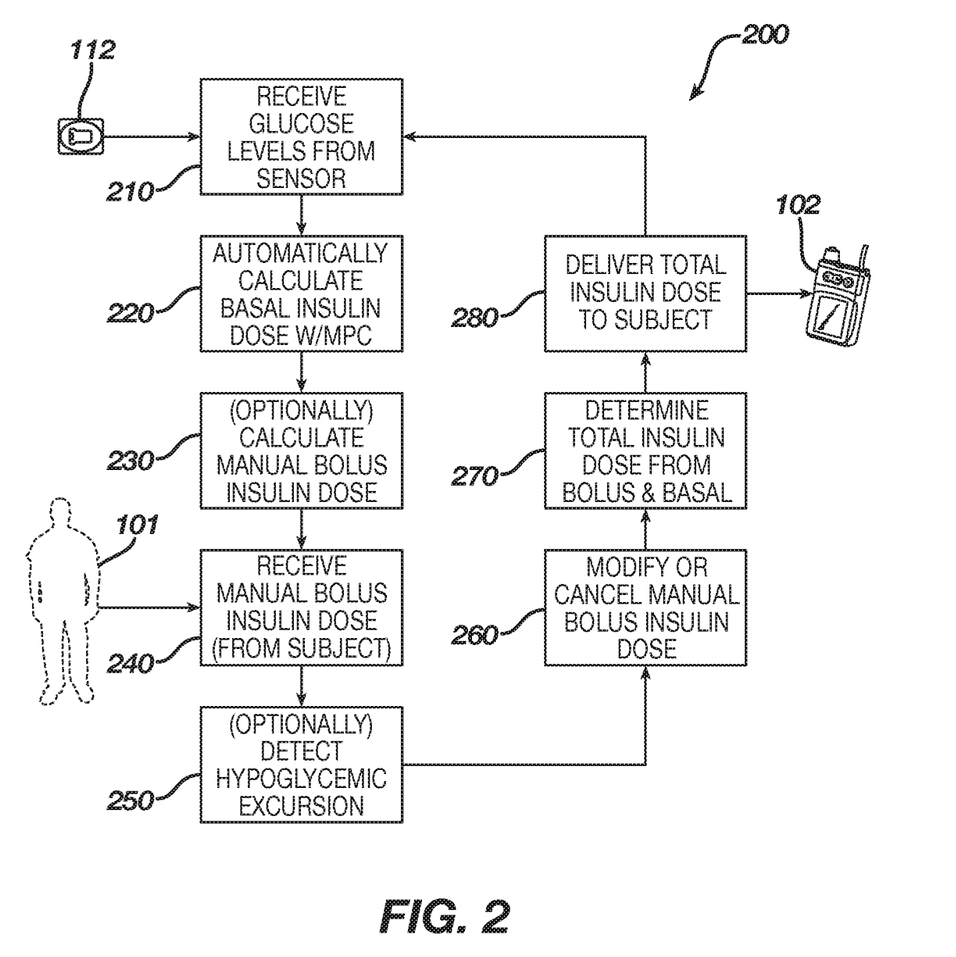
FIG. 2 illustrates a method for managing diabetes using automatic basal and manual bolus insulin control, in accordance with aspects of the present disclosure.

Described now with respect to FIG. 2 is a method 200 for managing diabetes of the subject 101. As explained above with respect to FIG. 1, the method 200 may be implemented on a single multi-functional unit or may operate on one or more of the controller 104, the delivery device 102, or the sensor 112, depending upon the specific implementation, the need for portability, or other factors. The delivery device 102 may be used for delivering insulin to the subject 101, and the glucose sensor 112 may be used for measuring glucose levels of the subject 101.

In one example, the method 200 uses both automatic basal insulin control and manual bolus insulin control. The automatic basal insulin control may be provided in the form of feedback controller with an MPC or a PID controller, or any other automated strategy for autonomously managing insulin infusion in conjunction with the measurement of glucose levels. In another example, rather than fully automated basal insulin control, the method 200 may be used with either manual insulin injections, manual glucose measurement, or both. In a similar manner, the method 200 may be used with different forms of bolus insulin control. For example, fully manual bolus insulin control may be employed in which a subject calculates the insulin bolus, e.g., before a meal, and manually injects the insulin. In another example, the bolus insulin control may be partially manual and partially based on calculations. For example, the subject can input certain information regarding a meal into the system and the system, e.g., the delivery device 102, can calculate the target insulin bolus dose.

Turning now to a more specific example, the method 200 at block 210 receives glucose levels of the subject 101 from the glucose sensor 112, e.g., on an ongoing basis. For example, a continuous glucose monitoring strategy may include receiving measurements as often as one or more times per minute or other predetermined interval (e.g., every five (5) minutes). Next, the method 200 at block 220 automatically calculates a basal insulin dose using MPC.

Figure 3:
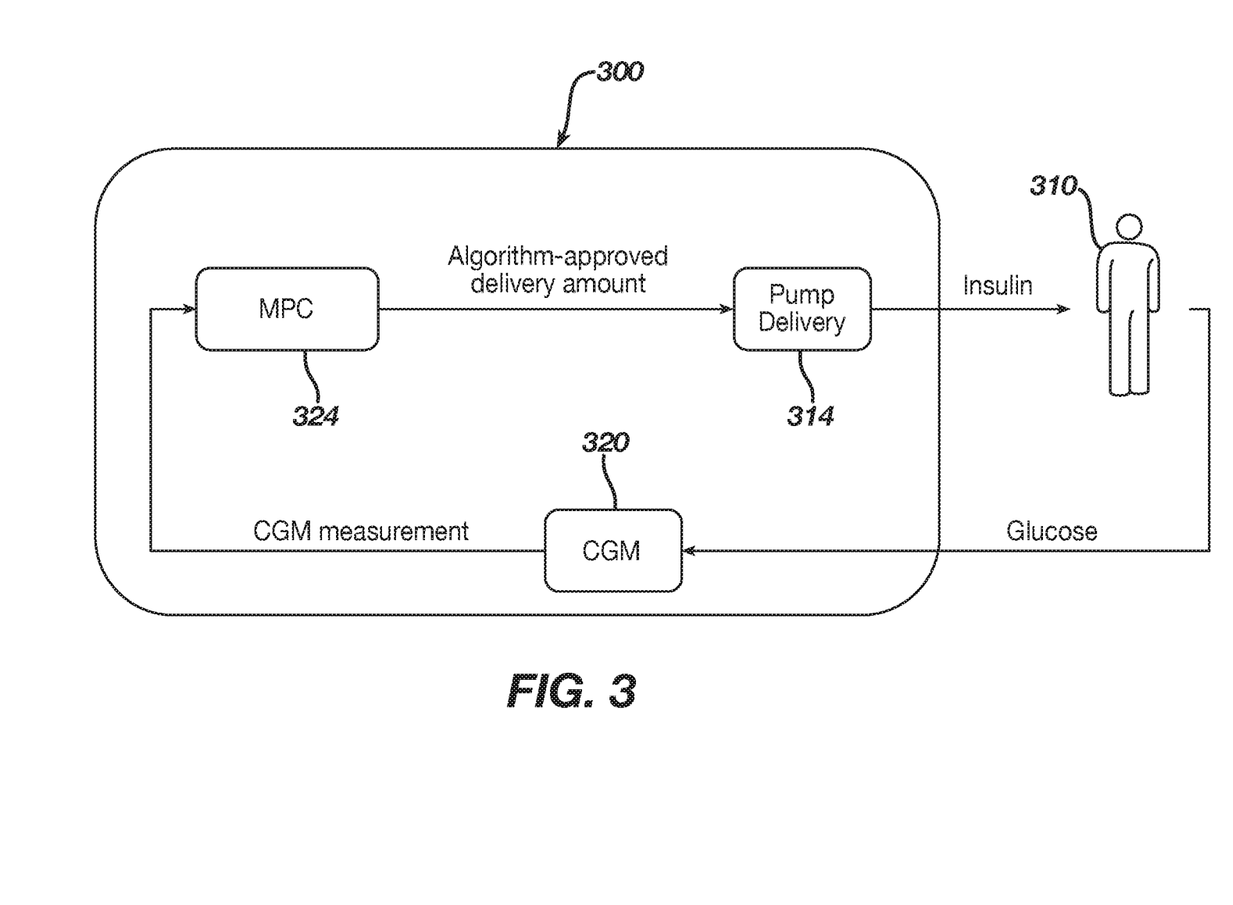
FIG. 3 illustrates a selected embodiment of a drug delivery device useful in the invention.

An exemplary drug delivery device 300 for use in the invention is shown in FIG. 3 and houses a pump delivery module 314, CGM module 320 and an MPC module 324. Preferably, this embodiment employs a hypoglycemia-hyperglycemia minimizer ("HEM") system as, for example, disclosed in U.S. Pat. No. 8,526,587 and U.S. patent application Ser. No. 14/015,831, both of which are incorporated in their entireties herein by reference, each being integrated within the housing of the drug delivery device. The CGM module 220 is configured for receiving signals from the CGM sensor 112 of FIG. 1, placed on the patient 310. The MPC module 324 is operatively connected to the CGM module as well as the pump delivery module and is configured to receive subcutaneous glucose information for providing the same to a stored algorithm, which is also made aware of all previous deliveries of insulin. This data is used to calculate near-future predictions of glucose levels and produce an insulin delivery rate that would mitigate the near-future predicted, or actual, hyper- or hypoglycemic conditions. The rate is then actuated by the pump delivery module 314 relative to the patient set rate corresponding to the current (e.g., 5 minute) interval. This protocol is repeated for each subsequent time interval.

Exemplary algorithms for use in the MPC module are detailed in U.S. Pat. Nos. 8,562,587 and 8,762,070 and U.S. application Ser. Nos. 13/854,963 and 14/154,241, the entire contents of which are herein incorporated by reference, creating predictive values for controlling the delivery of insulin based on basal rate, meal activities and continuous glucose monitoring. Technically, CGM is conducted according to a periodic schedule (e.g., once each five minutes). As noted above, insulin is delivered to the patient in this embodiment and for all following portions of this discussion using the HEM system. However and as noted previously, other known MPC or PID type delivery systems and predictive algorithms employed thereby can be utilized.

The MPC makes use of physiological data of the subject. For example, the physiological data includes desired glucose levels of the subject that have been previously programmed into the system. The data also includes previously delivered insulin amounts and previously measured glucose levels, and further analysis such as rates of change of insulin or glucose. As explained above, the basal insulin control allows for a steady state control of the subject so that glucose levels are maintained in a normal band as determined in consultation with the subject's physician. But the basal insulin control does not take into account various meal events, and meal information is not necessarily known to the system, unless it has been entered into the system. For example, optionally, the method 200 at block 230 calculates the manual bolus insulin dose, performing the function of a bolus calculator. In such a case, the system can take into account the target glucose level, glucose sensitivity of the subject, and known on-board level of insulin of the subject to make the calculation.

Alternatively, in one embodiment, the method 200 at block 240 receives a manual bolus insulin dose initiated by the subject 101, instead of using a bolus calculator function to determine the dosage. Whether the manual bolus insulin dose is calculated by an integrated bolus calculator by the method 200 at block 230 or fully manually entered by the subject 101 to the method 200 at block 240, the manual bolus insulin dose represents a departure from the basal insulin delivery of the control algorithm. Specifically, the subject 101, who is aware of an impending meal, makes a determination that a bolus of insulin is needed. However, the subject 101 is not necessarily aware of the current status of the basal insulin control.

Advantageously, the system is capable of taking this manual bolus dose and managing it in light of the current basal insulin control status. For instance, in one embodiment, the method 200 at block 250 may have detected a potential upcoming hypoglycemic excursion of the subject 101. For example, the hypoglycemic excursion may be indicated by the MPC based on the rate of glucose change of the subject, the previous insulin delivery levels, or the like. In such a case, allowing the manual dose of insulin to be delivered to the subject 101 could have deleterious consequences. It is a discovery of the invention that, in such a situation, patient health may be improved in comparison with conventional MPC techniques by canceling the manual bolus insulin dose. From the subject 101 viewpoint, this could be indicated via the user interface, and explained to the subject so that the subject is aware that the desired manual bolus insulin dose has been contemplated and rejected by the system and that the subject 101 may confidently continue with the meal without worry.

In another example, the method 200 at block 260 modifies the manual bolus insulin dose based on the physiological data of the subject, instead of cancelling or overriding the manual bolus insulin dose in its entirety. For example, after calculating a function of a difference between a present glucose level of the subject and a target glucose level of the subject, and taking account of the glucose sensitivity and the insulin-on-board, or after accounting for the present glucose rate of change of the subject 101, the method 200 can reduce the calculated dosage to a level that avoids any hypoglycemic incidents or excursions. One way of characterizing the modification process is that the MPC control has been modified to take into account the extra data sources relative to the manual bolus dosage, so that the method 200 is a method of using an enhanced MPC control that manages both basal and bolus insulin control of the subject 101. Another way of characterizing the modification process is that the bolus calculator has been enhanced so that the method 200 embodies an enhanced bolus calculator that takes into account physiological data of the subject including ongoing glucose measurements, historical insulin doses, and rates of change thereof. Regardless of how the method 200 is characterized, the advantages of combining bolus and basal insulin control allow the subject 101 better control of glucose level on an ongoing basis, even including during meal events.

Continuing now with the example of FIG. 2, the method 200 at block 270 determines a total insulin dose based on the modified manual bolus insulin dose and the calculated basal insulin dose. For example, during many iterations of the flow chart depicted in FIG. 2, there may have been no manual bolus insulin dose. In such cases, the total insulin dose may be the same as the calculated basal insulin dose in accordance with the MPC model. During other iterations of the flow chart of FIG. 2, manual boluses of insulin may be initiated by the subject 101. In such cases, the method 200 makes a determination of the appropriate insulin dose taking into account the physiological data, the bolus calculator data, or the like. Note that the term "total insulin dose" is not limited to adding the modified manual bolus insulin dose and the calculated basal insulin dose, and may be determined mathematically based on trending algorithms, look-up tables determined through clinical trials and programmed into the system, etc.

Next, the method 200 at block 280 commands the delivery device 102 to deliver the total insulin dose to the subject for that iteration of the flow chart 300. Thereafter, the method 200 returns to block 210 to reiterate the continuous feedback control described above.

Next, a specific working example will be given for illustration. A patient may have an insulin sensitivity factor ("ISF") of 1 unit:50 mg/dL, a target glucose level of 100 mg/dL, and a range of 90-180 mg/dL to which the MPC controller seeks to control glucose.

At one iteration of the control loop of the method 200, current data and conditions may be as follows: CGM reports 130 mg/dL and falling; test meter reports blood glucose of 130 mg/dL; IOB is 0.2 units; carbohydrates ("CHO") is 0 g (i.e., at the moment there is no meal). In addition, the MPC is currently predicting low glucose (below 90 mg/dL, the low end of the range), and therefore is withholding delivery of some or all insulin relative to the as-scheduled basal rate.

In one specific working example, a patient can decide to deliver a bolus of insulin, and inputs the following information to a bolus calculator: blood glucose ("BG")=130 mg/dL; CHO=0 g. In this example, the bolus calculator will suggest an insulin bolus using the following calculation:

$$\text{Correction} = \frac{BG - \text{Target}}{ISF} - IOB = \frac{130 - 100}{50} - 0.2 \text{ u} = 0.4 \text{ u}$$

However, because the method 200 is aware that the MPC is predicting low glucose of 90 mg/dL, the method 200 will suggest a new correction of zero:

Suggested Correction=0 u

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

The corresponding structures, materials, acts, and equivalents of all means or step plus function elements in the claims below, if any, are intended to include any structure, material, or act for performing the function in combination with other claimed elements as specifically claimed. The description set forth herein has been presented for purposes of illustration and description, but is not intended to be exhaustive or limited to the form disclosed. Many modifications and variations will be apparent to those of ordinary skill in the art without departing from the scope and spirit of the disclosure. The embodiment was chosen and described in order to best explain the principles of one or more aspects set forth herein and the practical application, and to enable others of ordinary skill in the art to understand one or more aspects as described herein for various embodiments with various modifications as are suited to the particular use contemplated.

What is claimed is:

1. A diabetes management system comprising:
    a delivery device for delivering insulin to a subject;
    a glucose sensor for measuring glucose levels of the subject;
    a bolus calculator for determining a manual bolus insulin dose based on physiological data of the subject, the bolus calculator being configured to calculate the manual bolus insulin dose as a function of a difference between a present glucose level and a target glucose level, a glucose sensitivity of the subject, and an on-board level of insulin of the subject; and
    a controller configured to:
        receive glucose levels of the subject from the glucose sensor on a periodic basis,
        automatically calculate a basal insulin dose using a model predictive control (MPC) algorithm and physiological data of the subject including desired glucose levels, amounts of the delivered insulin, and the measured glucose levels of the subject,
        receive the manual bolus insulin dose determined by the bolus calculator,
        predict, using the MPC algorithm, whether there will be a near-future glycemic excursion of the subject based on the physiological data including a rate of change of glucose in the subject that is indicative of hypoglycemia,
        modify the manual bolus insulin dose determined by the bolus calculator based on the determination of a predicted near-future glycemic excursion by the MPC algorithm that is indicative of hypoglycemia, wherein the modifying comprises overriding the manual bolus amount determined by the bolus calculator by reducing or canceling the manual bolus insulin dose determined by the bolus calculator if the near-future glycemic excursion indicative of hypoglycemia is determined,
        determine a total insulin dose based on the modified manual bolus insulin dose and the calculated basal insulin dose, and
        deliver the total insulin dose to the subject.

2. A diabetes management system with automatic basal and manual bolus insulin control, the diabetes management system comprising:
    a delivery device for delivering insulin to a subject;
    a glucose sensor for measuring glucose levels of the subject;
    a bolus calculator configured to determine a manual bolus insulin dose; and
    a controller configured to:
        receive glucose levels of the subject from the glucose sensor on a periodic basis,
        automatically calculate a basal insulin dose using a model predictive control (MPC) algorithm and physiological data of the subject including desired glucose levels, amounts of the delivered insulin and the measured glucose levels of the subject,
        receive the manual bolus insulin dose determined by the bolus calculator,
        predict, using the MPC algorithm, a near-future glycemic excursion of the subject based on the physiological data including a rate of change of glucose in the subject, the excursion being indicative of hypoglycemia,
        modify the manual bolus insulin dose based on the determination of a predicted near-future glycemic excursion by the MPC algorithm, wherein the modifying comprises reducing or canceling the manual bolus insulin dose determined by the bolus calculator based on a determination of the rate of change of glucose indicative of hypoglycemia from the predicted near-future glycemic excursion determined by the MPC algorithm.

3. The diabetes management system of claim 2, wherein the controller is further configured to determine a total insulin dose based on the modified manual bolus insulin dose and the calculated basal insulin dose.

4. The diabetes management system of claim 2, wherein the controller is further configured to command the delivery device to deliver the total insulin dose to the subject.

5. The diabetes management system of claim 2, wherein the manual bolus insulin dose is calculated as a function of a difference between a present glucose level of the subject and a target glucose level of the subject, a glucose sensitivity of the subject, and an on-board insulin level of the subject.

6. The diabetes management system of claim 2, wherein the modifying comprises overriding the manual bolus insulin dose determined by the bolus calculator.

7. A method for managing diabetes using automatic basal and manual bolus insulin control in an artificial pancreas system having:
- a delivery device for delivering insulin to a subject and a glucose sensor for measuring glucose levels of the subject, the method comprising the steps of:
- receiving glucose levels of the subject from the glucose sensor on a periodic basis;
- automatically calculating a basal insulin dose using a model predictive control (MPC) algorithm and physiological data of the subject including desired glucose levels, amounts of the delivered insulin and the measured glucose levels of the subject;
- using an integrated bolus calculator, determining a manual bolus insulin dose based on physiological data of the subject;
- receiving the determined manual bolus insulin dose;
- using the MPC algorithm, determining whether there will be a near-future glycemic excursion of the subject based on the physiological data including rate of change of glucose, the near-future glycemic excursion being indicative of hypoglycemia;
- if a determination is made that there will be a near-future glycemic excursion indicative of hypoglycemia, then modifying the manual bolus insulin dose of the bolus calculator, wherein the modifying comprises reducing or canceling the manual bolus insulin dose determined by the bolus calculator;
- determining a total insulin dose based on the modified manual bolus insulin dose and the calculated basal insulin dose; and
- commanding the delivery device to deliver the total insulin dose to the subject.

8. The method of claim 7, wherein modifying the manual bolus insulin dose comprises calculating a function of a difference between a present glucose level of the subject and a target glucose level of the subject, a glucose sensitivity of the subject, and an on-board insulin level of the subject.

9. The method of claim 7, wherein automatically calculating the basal insulin dose comprises using the model predictive control of the subject further based on a rate of glucose change of the subject, and the modifying comprises reducing the manual bolus insulin dose to account for the rate of glucose change.

10. The method of claim 7, further comprising, using the bolus calculator, calculating the manual bolus insulin dose to achieve a target glucose level as a function of a difference between a present glucose level and the target glucose level, a glucose sensitivity of the subject, and the on-board level of insulin of the subject.

* * * * *